United States Patent
Tanaka et al.

Patent Number: 5,613,849
Date of Patent: Mar. 25, 1997

[54] DENTAL CARE MATERIAL AND MANUFACTURING METHOD

[75] Inventors: Naoki Tanaka; Hiroshi Ohtsubo, both of Suwa; Michio Ito, Siojiri, all of Japan

[73] Assignees: Injex Corporation; Matsumoto Dental College, both of Nagano-ken, Japan

[21] Appl. No.: 378,450

[22] Filed: Jan. 25, 1995

[30] Foreign Application Priority Data

| Jan. 27, 1994 | [JP] | Japan | 6-007892 |
| Oct. 25, 1994 | [JP] | Japan | 6-260642 |

[51] Int. Cl.$^6$ ................................ A61K 6/00
[52] U.S. Cl. ................ 433/8; 433/9; 428/469; 428/472; 420/417; 420/420; 420/421
[58] Field of Search .................. 420/417, 470, 420/421; 428/469, 472; 433/8, 9

[56] References Cited

U.S. PATENT DOCUMENTS

| 4,404,166 | 9/1983 | Wiech, Jr. | 419/36 |
| 4,857,269 | 8/1989 | Wang et al. | 420/417 |
| 4,889,170 | 12/1989 | Mae et al. | 420/420 |
| 5,176,762 | 1/1993 | Berczik | 420/421 |
| 5,232,361 | 8/1993 | Sachdeva et al. | 433/8 |

FOREIGN PATENT DOCUMENTS

| 0356131 | 2/1990 | European Pat. Off. |
| 4032570 | 4/1992 | Germany |
| 05257091 | 10/1993 | Japan |
| WO92/16159 | 10/1992 | WIPO |

OTHER PUBLICATIONS

Noort, Van R., *J. of Mat. Sci.*, "Review Titanium: The Implant Material of Today", Nov. 1987, p. 3805, para. 1, right col.; p. 3808, para. 1, right col.; p. 3808, para. 1, left col.

*Primary Examiner*—Archene Turner
*Attorney, Agent, or Firm*—Oliff & Berridge

[57] ABSTRACT

A dental care material comprising a titanium sintered body has no harmful effects on the human body and easily produces products with complicated shapes having a high level of strength. A mixture of titanium powder and an organic binder is injection molded and subjected to binder removal and sintering processes to form a bracket for orthodontic or dental implant materials. Pure titanium powder, with an average granule diameter of no more than 40 μm, a carbon content by weight of no more than 0.3%, and an oxygen content by weight of no more than 0.6%, preferably is used to produce a titanium sintered body of combined carbon and oxygen content by weight of no more than 1.0%. Colored layers can be formed on the surface of the titanium sintered body using various methods as needed.

18 Claims, 5 Drawing Sheets

DENTAL CARE MATERIAL AND MANUFACTURING METHOD

BACKGROUND OF THE INVENTION

1. Field of the Invention

The present invention is concerned with a dental care material and a method for producing the material. It is especially concerned with a material suited for orthodontic appliances and dental implantation.

2. Description of Related Art

Among the materials used in a human mouth are wire and brackets for orthodontics and dental implantation. Depending on the use, plastics, ceramics, and stainless steel, etc., have traditionally been the most commonly used materials. In some cases utilization has been made of Ti—Ni system alloys, Ni—Cr system alloys, and Fe—Ni—Cr system alloys. However, there is an increasing number of patients who suffer from metal allergies, caused by a particular metal touching and irritating the skin and causing roughness or inflammation. Among such metal allergies are skin allergies caused by earrings, necklaces, and other accessories, and allergies caused in the mouth by the metals used in dental care. No one metal is the cause of the allergies, and individuals differ in regard to which types of metal cause allergies. More serious than allergies is the carcinogenic nature of such metals as Ni and Cr. The use of Ni—Cr system alloys on a living human body is even prohibited in some countries.

With each of the dental care materials mentioned above there are problems, such as mechanical characteristics, production costs, the elution of the material into the body, compatibility with living tissues, etc. For example, plastics may break due to lack of strength; ceramics are too expensive; stainless steel results in too much elution, which, like the alloys mentioned above, may cause problems such as allergies and cancer.

In addition, from the molding material perspective, brackets and dental implantation have traditionally been produced by the casting method and mechanical processing. With the casting method, the problem of breakage during use often occurs due to defective casting, especially due to the formation of casting pockets. In addition, the creation of complicated shapes is difficult in casting due to the problem of running liquid. For example, the shape of the surface of a bracket to be bonded to teeth, or the shape of the screw component for an implant material, is too complicated to be produced exactly as designed. Thus, in the case of the bracket, there is insufficient bonding strength. In regard to the dental implantation, after implanting an implant material, the screw may loosen causing breakage of the upper structure or a mismatching bite, resulting in difficulty in chewing food.

On the other hand, when the process involves mechanical processing, such as cutting, there is difficulty in processing materials with a high level of hardness, especially titanium materials that have poor machine processability, resulting in products with poor precision. For example, the screw component of a dental implantation must be mechanically processed because it cannot be produced by casting. Poor precision in the screw component can allow the entrance and spread of infectious agents to the screw component, which is screwed inside the mandibula. These infectious agents include Escherichia coli, Candida, Pseudomonas aeruginosa, staphylococcus, and aureus, which cause halitosis and susceptibility to gum diseases.

SUMMARY OF THE INVENTION

The present invention aims to solve the above problems by providing dental care materials, such as bracket and dental implant materials made of titanium, which are harmless to the human body, yet easily and inexpensively form molds of delicate and complicated shapes.

A further object of embodiments of the present invention is to produce a material having the strength and ductility required for dental care materials in addition to having an exterior appearance desirable for dental care materials, such as a desirable color.

The dental care material of embodiments of the present invention comprises a sintered body wherein the body is a molded mixture of titanium material and an organic binder, which is sintered after removing the binder (de-binding).

In an embodiment of the present invention, the sintered body has a carbon content of no more than 0.5% by weight.

In another embodiment, the sintered body has an oxygen content of no more than 0.8% by weight.

In a further embodiment, the combined carbon and oxygen content of the sintered body is no more than 1.0% by weight.

In another embodiment, the titanium sintered body is molded with titanium powder having an average granule size of no more than 40 μm.

In any of the above embodiments, a colored layer may be formed on the surface of the sintered body. The colored layer may be formed by an ion plating method, an anodic oxidation method, a heat treatment method, or a heat spraying method. Preferably the ion plating method is used.

Furthermore, a gold layer or a gold-palladium alloy layer may be formed on top of the colored layer.

According to embodiments of the present invention, the sintered body may be molded as a bracket or as a dental implant material, for example.

Next, regarding the method for producing the dental care material, titanium powder and an organic binder are mixed to form an injection molding compound, which is molded to produce a molded body. After removal of the binder from the molded body, a titanium sintered body is produced by sintering.

In an embodiment of the present invention, the titanium powder used has a carbon content of no more than 0.3% by weight and an oxygen content of no more than 0.6% by weight, with an average granule diameter of no more than 40 μm.

Moreover, a colored layer may be formed on the surface of the sintered body after sintering. The colored layer may be formed using an ion plating method, an anodic oxidation method, a heat treatment method, or a heat spraying method, with ion plating being the preferred method.

In this instance, a gold layer or a gold-palladium alloy layer may be formed on top of the colored layer.

In forming a colored layer using a heat spraying method, the colored layer may be formed by spraying $Al_2O_3$ or $TiO_2$ powder.

Embodiments of the present invention can provide a practical, high quality dental care material wherein there are fewer incidents of damage caused by breakage and chipping, which occurs easily in materials formed by traditional casting methods, and wherein delicate and complicated shapes can be formed easily, and precise shapes can be created at low cost, which has been impossible to accomplish with traditional mechanical processing methods.

Materials with a high degree of strength and ductility are formed as a result of reducing the carbon or oxygen content below a specified amount.

A decline in breakage strength is prevented by raising the density of the titanium sintered body to no less than 95% by using titanium powder having an average granule diameter of no more than 40 μm, thus preventing poor coupling. By "density" the application means the opposite of "porosity," i.e., a density of 100% means there are no pores.

The ductility of a sintered body can be raised by regulating the granule diameter of titanium powder as well as the carbon and oxygen content, thus producing a dental care material with a high level of strength.

A colored layer with a high degree of bonding strength can be obtained by an ion plating method, thus resulting in the formation of a highly durable and long-lasting colored layer.

Colors corresponding to types of metal can be obtained by forming a metal film on top of the colored layer. Various colors close to the desired color, including a white color close to that of the human tooth, can be obtained.

BRIEF DESCRIPTION OF DRAWINGS

The invention will be described in conjunction with the following drawings in which like reference numerals designate like elements and wherein.

DETAILED DESCRIPTION OF PREFERRED EMBODIMENTS

The dental care material and the method of producing the material according to the present invention are described in detail hereafter with reference to the drawings. The material formed according to the present invention may be used as a bracket or as dental implant materials, for example. Moreover, in the present invention, titanium may be used as a raw material or as a component part. Titanium, being inert to the human body in its pure form or in alloy form, can be used widely as a medical material such as a support or prosthesis for a broken bone.

Figure 1:
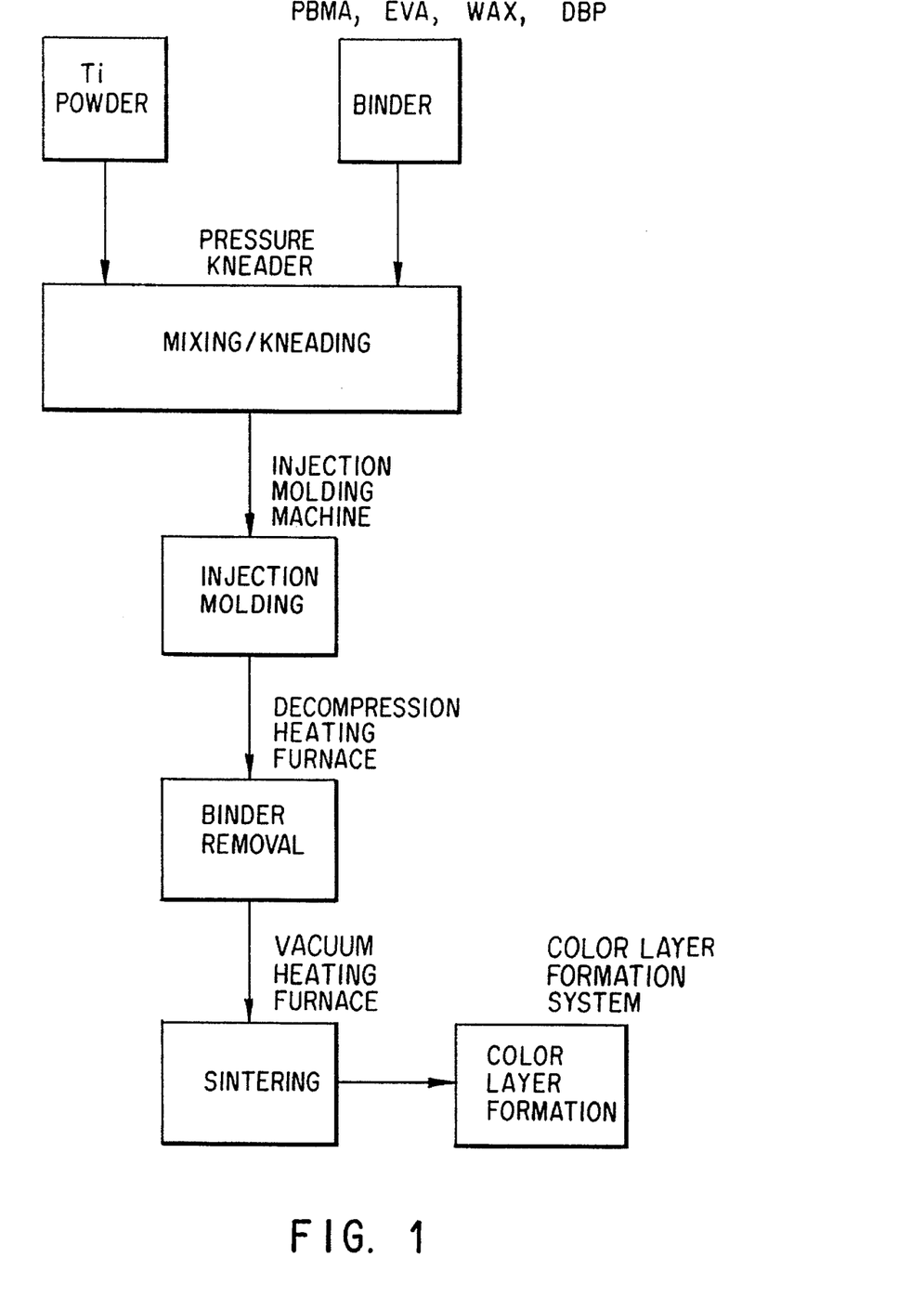
FIG. 1 is a flowchart showing the manufacturing process applicable to each embodiment of the present invention.

FIG. 1 shows the process of manufacturing the material according to an embodiment of the present invention. The process begins with forming the injection mold compound by mixing titanium powder and an organic binder. The titanium powder preferably is pure titanium powder produced by the gas-atomizing method. The titanium powder usually comprises carbon and oxygen. The carbon content and the oxygen content of the dental care material have a great effect on the ductility of the material, which will be explained further hereafter. Therefore, the carbon content and the oxygen content of the titanium powder preferably are controlled within certain limits.

In the process to be explained in detail below, some amount of carbon occasionally enters the sintered body from the residue resin during the time of sintering. However, the amount of carbon in the sintered body to be formed during the final stage of the process can be made nearly equal to the amount of carbon contained in the titanium powder. On the other hand, oxygen may enter the sintered body during each of the heating steps explained below. Thus, the oxygen content of the sintered body is determined by adding the amount of entering oxygen to the oxygen contained in the titanium powder. However, the amount of oxygen can be reduced by preventing oxygen from entering into the sintered body during the production process. With the establishment of a production process in which the amount of oxygen entering the body is relatively small, the amount of oxygen in the final sintered body can be sufficiently low if the amount of oxygen initially contained in the original titanium powder is small.

For the organic binder, a binder system having at least two binder components is used. Preferably, a substance whose main components are thermoplastic resin and wax is used with the addition of a plastic agent, a lubricant, a binder removal promotion agent, a mold release agent, and a surfactant, as needed. The amount of organic binder should be determined properly according to the material, but, in general, it is 9%±1% by weight.

Next, injection molding is performed on the compound with an injection molding machine. Metal molds for molding are manufactured to form a bracket for a orthodontic appliance shown in FIGS. 2A–2C and for the dental implantation shown in FIG. 4.

Figure 2A:
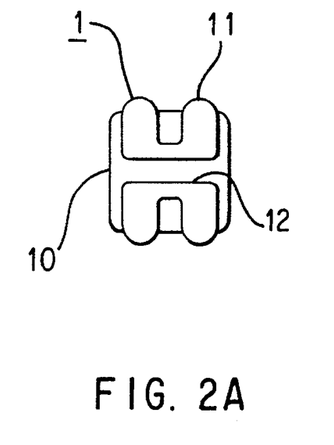
FIGS. 2A–2C are a front view, a cross section, and a back view, respectively, showing the shape of a brackets for orthodontics formed as an embodiment of the present invention.
Figure 2B:
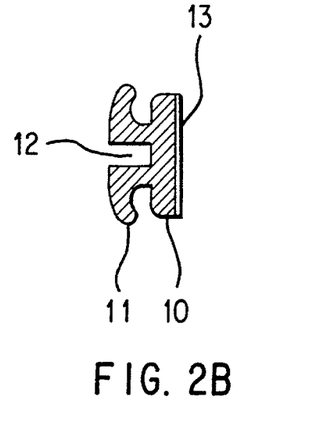
Figure 2C:
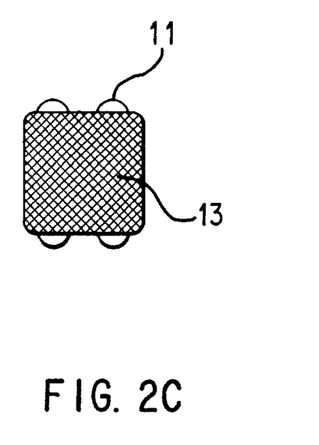
Figure 3:
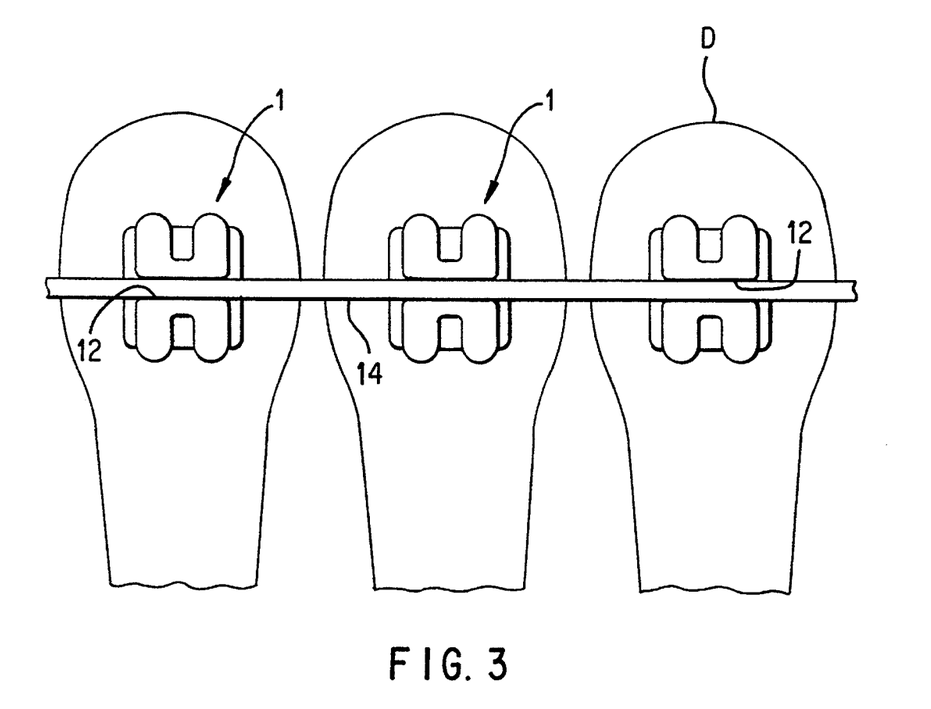
FIG. 3 is an illustration showing a condition wherein the brackets are mounted on teeth.

The bracket 1 for orthodontics shown in FIGS. 2A–2C is provided with a vertical pair of engagement components 11, 11, on the front side of the base component 10, an insertion groove 12 being provided between the pair of engagement components 11, 11. A lattice groove formation 13 is formed on the back side of the base 10, which is bonded to the surface of the tooth D shown in FIG. 3. In some cases, numerous dimples, in place of a lattice groove formation, are provided on the back side of the base 10, but a lattice groove formation works best, considering bonding strength. After bonding the bracket 1 to the surface of each of more than one tooth D using a bonding agent, a wire 14 is inserted in the insert groove 12 and pressure is applied so that the teeth D line up straight.

Figure 4:
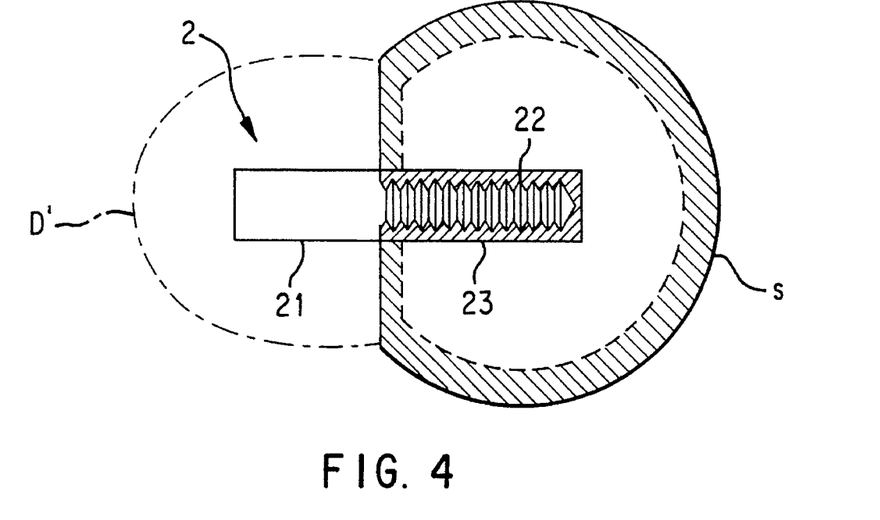
FIG. 4 is an illustration showing the shape of an dental implant material formed as an embodiment of the present invention and a mounting condition thereof.

The dental implant material 2 in FIG. 4 comprises a male screw unit having a head 21, a male screw component 22, and a female screw unit 23 having a female screw component; which is anchored securely by screwing the male screw component into the female screw unit 23 provided in a mandibula. All of elements 21, 22 and 23 may be made from the implant material of the present invention. At the same time, the crown D', which is cemented on head 21, is secured in place.

The molded bodies thus created for the respective purposes are sent to a decompression heating furnace where binder is removed from the bodies as shown in FIG. 1. During the binder removal process, heat is applied within a non-oxidation atmosphere or a decompression (i.e., vacuum) atmosphere or both to remove binder. If at least two of the binder components have different melting temperatures, the binder may be removed by raising the temperature of the molded body above the intermediate temperature at which the binder system flows, which is between the melting point of the various components. Binder will exude from the molded body wherefrom it can be removed. Since only the binder with the lowest melting temperature is initially removed, the intermediate temperature at which the binder system flows will increase. Therefore, it may be necessary to continually increase the temperature ensuring that it remains below the temperature of the highest melting point of a binder component. Alternatively, a specific solvent (liquid or gas) may be used to remove only a specific component in the binder.

Next, sintering takes place in the vacuum heating furnace. During the sintering process, a non-oxidation atmosphere or a vacuum atmosphere or both can be used.

The bracket and the dental implant material comprising titanium sintered bodies thus created reduce the problems of defective casting and running liquid of the traditional casting method. Hence the delicate and complicated shapes shown in FIGS. 2A–2C and in FIG. 4 can be easily realized. Furthermore, the desired strength is obtained by providing the binder removal and sintering processes. For example, the formation of a lattice groove formation on the back side of base 10 is not possible with the conventional casting method, which can at best provide relatively large dimples. To create small dimples or a lattice groove formation, conventionally a further cutting process or bonding to the unit is required after the casting or cutting process. Further, even if such a process is possible, the processing cost becomes extremely high. With the dental care materials of the present invention, a very fine lattice groove formation can be formed without problems, resulting in substantial savings in production costs.

Both the bracket and the dental implant materials mentioned above comprising titanium sintered bodies are used to anchor to teeth securely, requiring a certain level of strength (rigidity). Therefore, hardness and ductility (elongation) need to be controlled during the manufacturing process.

The quality of sintered bodies in preferred embodiments of the present invention is determined mainly by the level of ductility obtained in the body. The ductility of the titanium sintered body is determined by carbon content, oxygen content, and the density of the final sintered bodies. Small differences in the amount of carbon and oxygen in the titanium sintered body can change the hardness and ductility of the sintered body. When the amount of carbon increases, TiC (titanium carbide) is produced and ductility declines and hardness increases. Moreover, when the amount of oxygen increases, ductility declines, and hardness increases, due to a rise in the amount of solid solution hardening.

Figure 5:
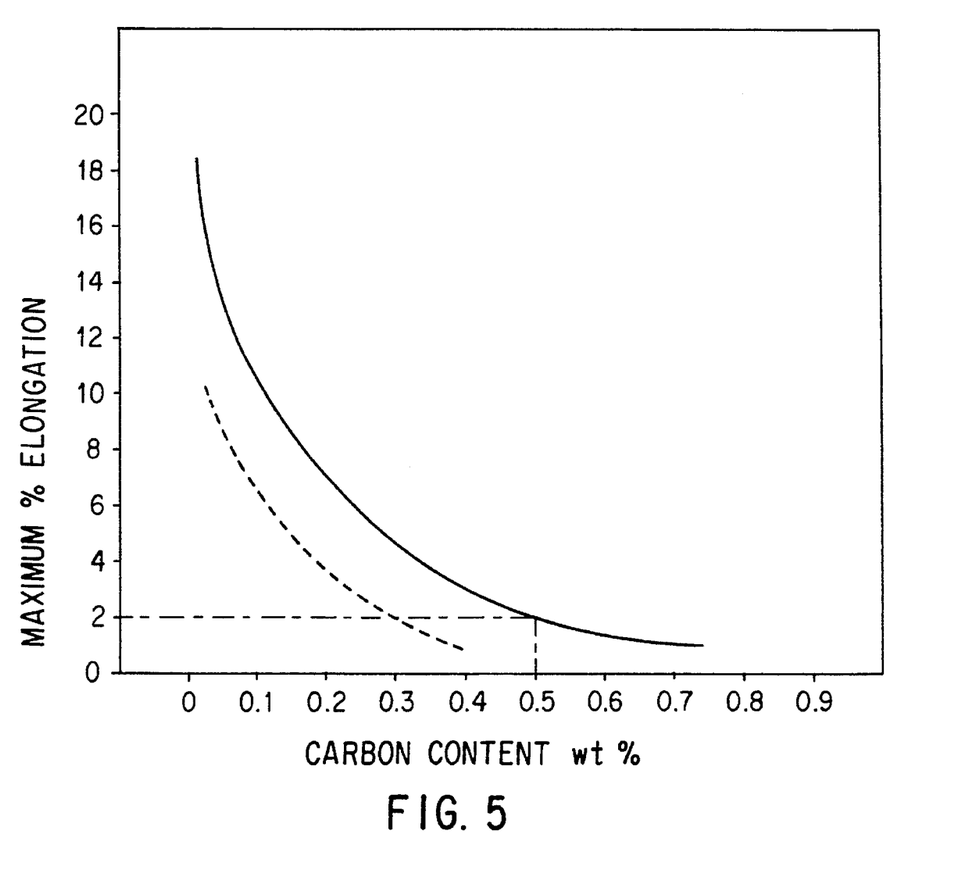
FIG. 5 is a graph showing the relationship between the carbon content of titanium powder and the maximum % elongation of the titanium sintered body.
Figure 6:
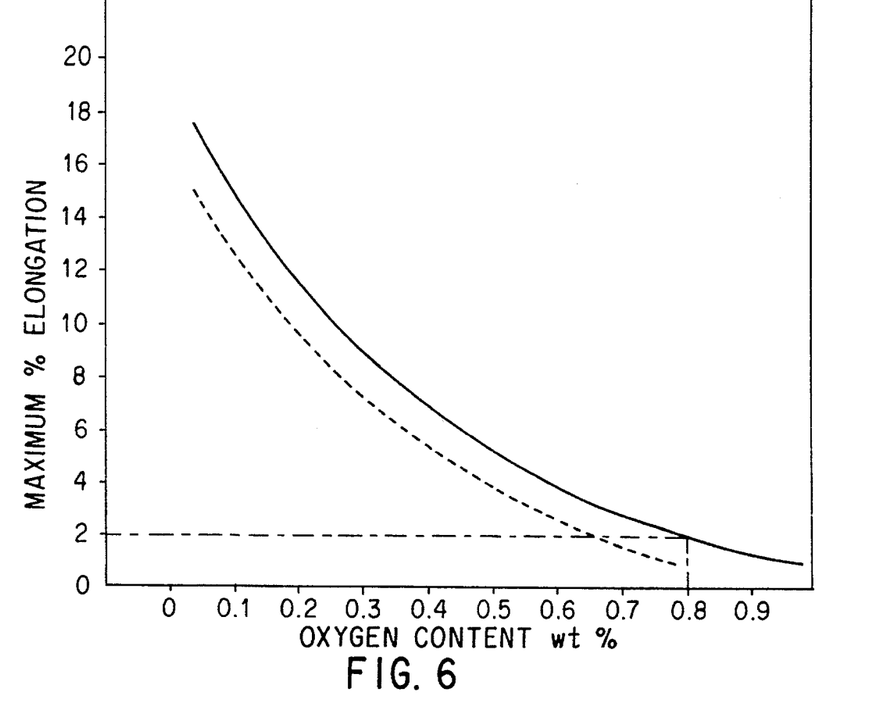
FIG. 6 is a graph showing the relationship between the oxygen content of the titanium powder and the maximum % elongation of the titanium sintered body.

FIG. 5 and FIG. 6 show the relationship between the carbon content and the oxygen content, respectively, in the titanium sintered body and the maximum amount of elongation. The ductility of the material is determined by the amount of elongation tensile that results when subjected to a elongation test. The values representing the relationship between the carbon content and the amount of elongation shown in FIG. 5 are determined from the average values obtained using titanium powder with an oxygen content of 0.3% to 0.5% by weight. In FIG. 5, the solid curve represents the carbon content in the titanium sintered body, while the dotted curve represents the carbon content in raw titanium powder used to form the sintered titanium body. On the other hand, the values representing the relationship between the oxygen content and the amount of elongation shown in FIG. 6 are determined from average values obtained using titanium powder with a carbon content of 0.1% to 0.3% by weight. In FIG. 6, the solid curve represents the oxygen content in the titanium sintered body while the dotted curve represents the oxygen content in raw titanium powder used to form the sintered titanium body.

The elongation of materials used for dental care materials, especially for orthodontic or dental implant materials, should be around 2%, preferably 4% or more. If the elongation is below 2%, breakage or chipping occurs during treatment. Therefore, as the graphs indicate, the carbon content and the oxygen content of the raw titanium powder preferably should be-held to no more than 0.3% and 0.6% by weight, respectively. Preferably, the total amount of carbon and oxygen should be no more than about 0.5% by weight in the Ti powder. On the other hand, the carbon content and the oxygen content of the titanium sintered body preferably should be held to no more than 0.5% and 0.8% by weight, respectively, and the combined carbon and oxygen content of the sintered body preferably should be held to no more than about 1.0% by weight.

Titanium powder used for the dental care materials of the present invention contains minute amounts of carbon and oxygen, as explained above. The titanium powder is generally pure and any other impurities are generally minute and unavoidable. However, in recent years, the use of titanium alloy as an inert material for the human body is increasing. Such alloys, such as, for example, Ti-6Al4V alloy and Ti—Mo alloy, can also be used for molding the dental care materials of the present invention.

Figure 7:
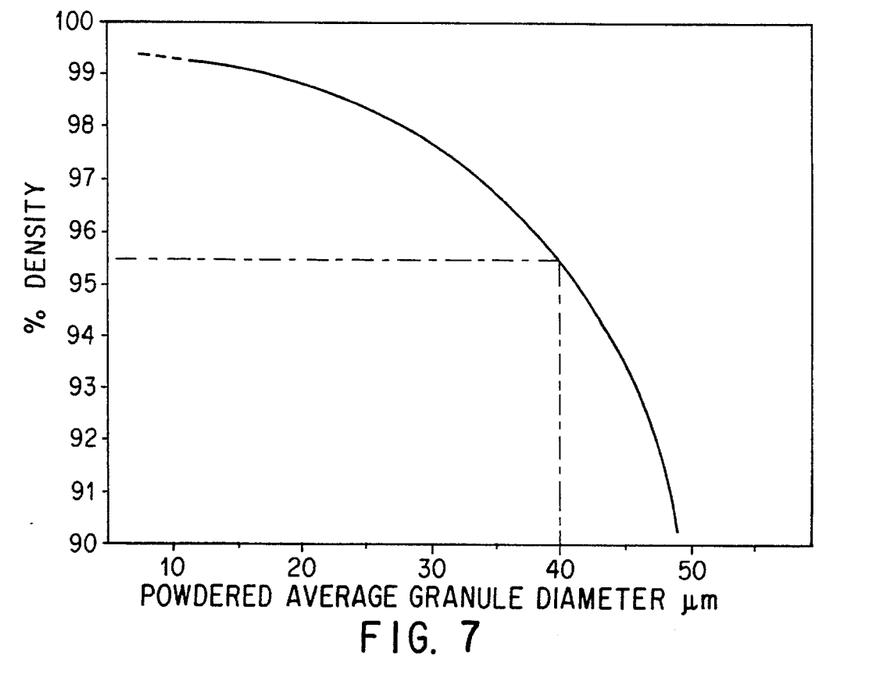
FIG. 7 is a graph showing the relationship between the average granule diameter of the titanium powder and the density of the titanium sintered body.

The relationship between the granule diameter of the titanium powder and the density of the sintered body is shown in FIG. 7. The density of the sintered body falls sharply when the granule diameter exceeds 40 μm. Therefore, the average granule diameter of the powder preferably should be no more than 40 μm in order to obtain a sintered body with a density of 95% or higher. A decline in density causes a sharp expansion in the cavity components due to poor coupling within the sintered body, resulting in a notch effect and in decreased ductility.

Figure 8:
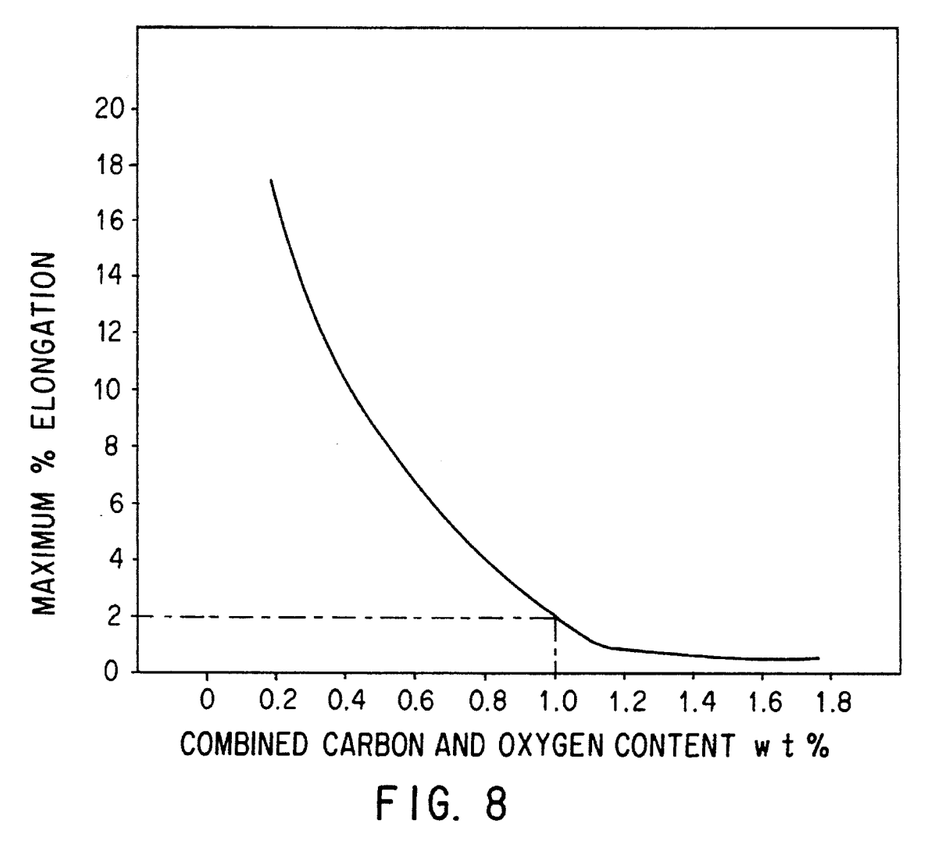
FIG. 8 is a graph showing the relationship between the sum of carbon content and oxygen content of the titanium sintered body and the maximum % elongation of the titanium sintered body.

FIG. 8 shows the relationship between the combined carbon and oxygen content of the titanium sintered body and the amount of elongation. As explained above, both the carbon content and the oxygen content affect the ductility of the material, and it appears that the ductility is increased by reducing the total carbon and oxygen content. The present invention allows for the formation of a dental care material with high rigidity, when the carbon content and the oxygen content of the titanium powder are maintained between about 0.05% and about 0.1% by weight and at about 0.1% by weight, respectively, and when the carbon content and the oxygen content of the titanium sintered body are controlled at about 0.15% and about 0.3% by weight, respectively. Preferably, the combined carbon and oxygen of the titanium powder is no more than about 0.5% by weight and the combined carbon and oxygen content of the sintered body is no more than about 1.0% by weight. The results of tests establishing the above characteristics in actual dental care materials will be described in detail hereafter.

The material and process of the present invention can be used for dental care materials other than orthodontic appliances and dental implantation. For example, the material and process can be used to make a connecting member, e.g., a hinge, for a removable artificial tooth, denture or bridge. These dental care materials differ from dental implantation as shown in FIG. 4 in that they are easy to remove, for cleaning, etc.

A colored layer may be formed on the surface of the sintered body. The colored layer may be formed by an ion plating method, an anodic oxidation method, a heat treatment method, or a heat spraying method.

Preferably the ion plating method is used. In the ion plating method, gas is discharged under a decompression atmosphere and a part of the substance is ionized to be vaporized in the gas. An electric field is applied to the ions to accelerate and bombard them onto the surface of a material to form a colored layer on the material. The heating methods used to vaporize the substance include, but are not limited to, an electron beam heating method, a hollow cathode discharge plasma electron beam method, and a sputtering vaporizing method. The ionizing methods include, but are not limited to, a glow discharge method, high frequency wave discharge, microwave discharge and other discharge methods, the heat electron method, the electron beam method, and other ionization methods in which electrons are supplied and bombarded from an outside source.

For example, the sintered body is attached to the cathode within the system and titanium is vaporized by a hollow cathode discharging plasma electron beam in a nitrogen atmosphere of about 0.0001 torr to ionize titanium with the nitrogen gas and deposit titanium nitride on the surface of the sintered body. In this manner, the sintered body can be colored gold, red, etc. For example, the various colors can be obtained by varying the amount and pressure of the gas flowing into the system. Furthermore, a gold layer or a gold-palladium alloy layer may be formed on top of the colored layer to form additional colors.

In the anodic oxidation method, a sintered body is attached to an anode and voltage is impressed within a boric acid electrolytic solution to form an oxidation film on the surface of the sintered body. Colors of yellow, green and red, etc., can be produced using the oxidation film.

In the heat treatment method, various colors are obtained by heating a sintered body to a specific temperature in various atmospheres.

In the heat spraying method, various colors are produced by coating the surfaces of a sintered body with various metal oxides and nitrate powders using a sprayer. The colored layer may be formed by spraying $Al_2O_3$ or $TiO_2$ powder.

EXAMPLES

Examples 1–6

Titanium powders A–F in Table 1 are used to form brackets in Examples 1–6, respectively. As the organic binder, PBMA (polybutylmethacryrate), EVA (ethylene vinyl acetic acid copolymer), wax, and DBP (dibutylphtarate) are used. The organic binder is mixed and kneaded with the titanium powder using a pressure kneader for 30 minutes at 130° C. to produce an injection molding compound. Injection molding is performed on the compound with an injection molding machine to form a bracket of FIGS. 2A–2C, having a very fine lattice groove formation. The conditions for molding are as follows: molding temperatures—150° C.; molding pressure—1,000 $kgf/cm^2$; and metal mold temperatures—20° C.

TABLE 1

|   | Carbon Content (wt %) | Oxygen Content (wt %) | Average Granule Diameter (μm) |
|---|---|---|---|
| A | 0.12 | 0.25 | 29 |
| B | 0.36 | 0.22 | 31 |
| C | 0.11 | 0.90 | 27 |
| D | 0.12 | 0.25 | 63 |
| E | 0.05 | 0.20 | 30 |
| F | 0.05 | 0.15 | 70 |

The molded bodies are then sent to a decompression heating furnace where the binder is removed. In order to remove the binder from the molded bodies, the pressure is set at 0.1 torr with a maximum heating temperature of 400° C., the maintenance time being one hour.

Next, sintering takes place in the vacuum heating furnace. Pressure is set at 0.1 to 0.0001 torr with a maximum heating temperature of 1250° C., the maintenance time being three hours to obtain a titanium sintered body. The titanium sintered bodies have a Vickers hardness of 180 to 220 Hv, have sufficient anti-wear characteristics, and have enough hardness to secure a smooth contact with wire.

Density measurement, strength testing, bonding strength testing, and elution testing are conducted for the produced brackets. The strength test is conducted by placing the bracket, with the back surface facing down, on a steel sheet, and by forcing displacement and deformation from above to determine the existence of breakage.

For the bonding strength test, one bracket is bonded to each of two teeth adjacent to each other and the two adjacent brackets are tightened by wire wrapped around the brackets. The bonding strength is evaluated by whether the brackets are separated from the teeth by tightening the wire.

The measurement of elution, or the amount of dissolved bracket entering the body, is performed by soaking the bracket in a 1% lactose solution for three days. The results of the measurements thus obtained are shown in Table 2, which are compared to measurements for Comparative Example 1, which has the same shape SUS316L bracket but has dimples on the back side of the base produced by a lost wax process.

TABLE 2

|  | Powder Type | Mechanical Strength | Adhesive Strength | Elution Amount $mg/cm^2$ |
|---|---|---|---|---|
| Example 1 | A | No breakage | No separation | 0.25 |
| Example 2 | B | Breakage | No separation | 0.28 |
| Example 3 | C | Breakage | No separation | 0.27 |
| Example 4 | D | Breakage | No separation | 0.26 |
| Example 5 | E | No breakage | No separation | 0.26 |
| Example 6 | F | Breakage | No separation | 0.26 |

TABLE 2-continued

| | Powder Type | Mechanical Strength | Adhesive Strength | Elution Amount mg/cm² |
|---|---|---|---|---|
| Comparative Example 1 | — | No breakage | Separation | 1.65 |

In Examples 1 and 5, the brackets formed do not have any problems in regard to mechanical strength and bonding strength. In both Example 2 and 3, the brackets have problems with breakage due to insufficient mechanical strength, although both have satisfactory bonding strength. In both cases, ductility appeared to have deteriorated due to the excessive carbon content in Example 2 and the excessive oxygen content in Example 3. Moreover, Examples 4 and 6 appear to have breakage problems due to numerous pores in the material resulting from a low sintering density caused by the use of coarse granules. Furthermore, in Comparative Example 1, the shape of the dimples on the surface contacting the tooth are not the specified shape, because they were produced by the lost wax process. This results in the separation of the bracket from the tooth due to weak bonding strength.

Regarding the elution test, all the brackets in Examples 1–6 result in sufficiently low values and are not inferior to titanium processed products produced by conventional mechanical manufacturing. However, the amount of elution of the stainless steel product in Comparative Example 1 produced by the lost wax process is substantially larger than the amount in Examples 1–6.

Examples 7–12

Next, the mixed compound of titanium powder and organic binder used in the above Examples 1–6 is injection molded to form the shapes illustrated in FIG. 4. The resulting molds are made into the dental implant material of Examples 7–12, respectively, after removing the binder and sintering under the same conditions as the above Examples 1–6, respectively.

Density measurements, strength testing, elution testing, and airtightness testing are conducted and the results are summarized in Table 3, which also includes the dental implant material of Comparative Examples 2 and 3, wherein a pure titanium rod and a stainless steel rod, respectively, were created by the casting method and were made into the screw shape of FIG. 4 by a mechanical process after casting.

TABLE 3

| | Powder Type | Mechanical Strength | Airtightness | Elution Amount mg/cm² |
|---|---|---|---|---|
| Example 7 | A | No breakage | No leakage | 0.26 |
| Example 8 | B | Breakage | No leakage | 0.29 |
| Example 9 | C | Breakage | No leakage | 0.28 |
| Example 10 | D | Breakage | No leakage | 0.27 |
| Example 11 | E | No Breakage | No Leakage | 0.27 |
| Example 12 | F | Breakage | No Leakage | 0.28 |
| Comparative Example 2 | — | Breakage | Leakage | 0.29 |
| Comparative Example 3 | — | No breakage | Leakage | 1.55 |

In the strength test, both ends of the material are securely anchored and force is applied vertically on the central component to give displacement (2 mm), and the material is then examined for the existence of cracks.

In the airtightness test, a hole is drilled in a mandibula in which the dental implant material is to be screwed. Then a titanium (this embodiment) or a stainless steel (Comparative Examples) tube is inserted in the hole. After screwing the screw component into the mandibula, air with a pressure of 10 atmospheres is blown through the tube to check for air leakage from the screw component.

With Examples 7 and 11, as was the case with Examples 1 and 5, there are no problems whatsoever. Example 8 and Example 9 have problems with breakage due to the high carbon and oxygen content like Example 2 and Example 3 above. Examples 10 and 12 also have problems with breakage due to low sintering density, as was the case with Examples 4 and 6 above. Comparative Example 2, for comparison, has problems with breakage due to lack of strength and problems with air leakage due to poor precision in the processing screw. Moreover, Comparative Example 3 has problems with air leakage and large amounts of elution caused by stainless steel.

According to Examples 1–12 above, a dental care material having delicate and complex shapes, which are impossible to produce using conventional casting methods and mechanical processing methods, can be formed with a high level of precision by first injection molding a compound formed by a mixture of titanium powder and an organic binder, and then by forming the titanium sintered body through a binder removal process and a sintering process. Moreover, the titanium sintered body has sufficient hardness and ductility to insure the required strength for a dental care material as well as a low level of elution, thus realizing a material with higher capabilities than conventional products.

Examples 13–22

Next, Examples 13–22 will be explained wherein a desired color is added by forming a color layer on the surface of the dental care material. In each Example, explained hereafter, the titanium sintered body is produced in the same manner as Examples 1–6 above using titanium powder with the carbon content, oxygen content and average granule diameter presented in Table 4. After the titanium sintered bodies are produced, color layers are formed on the surface of the sintered bodies using various methods as presented in FIG. 1.

TABLE 4

| Powder Type | Carbon Content (wt %) | Oxygen Content (wt %) | Average Granule Diameter (μm) |
|---|---|---|---|
| Gas Atomize Powder | 0.12 | 0.25 | 29 |

In Examples 13–15, an ion plating method is used to form a colored layer. The bracket is attached to the cathode within the system and titanium is vaporized by a hollow cathode discharging plasma electron beam in a nitrogen atmosphere of about 0.0001 torr to ionize titanium with the nitrogen gas and deposit titanium nitride on the surface of the sintered body.

In Example 13, the nitrogen gas flow is adjusted so that the partial pressure of nitrogen gas is at about 0.00001 torr and the temperature of the system is set at 300° C. with a processing time of about one hour. As a result, the surface of the sintered body is colored pink.

Further, by evaporating gold or an alloy consisting of 85% gold and 15% palladium on top of the titanium nitride layer with a heat temperature of 300° C. and a processing time of 15 minutes, additional colors can be obtained. In Example 14, by vaporizing gold on top of the titanium nitride layer, a color of yellow-white is obtained. In Example 15, by vaporizing the gold-palladium alloy, a color of silver-white is obtained.

Each of the materials of Examples 13–15 are soaked in a 1% lactose solution for three days to examine the elution, the results of which are compiled in Table 5. The brackets in Examples 13–15 are found to possess sufficient characteristics required for an orthodontic material. The bracket in Comparative Example 4 was produced by casting stainless steel.

TABLE 5

|  | Production Method | Surface Color | Elution Amount $mg/cm^2$ |
|---|---|---|---|
| Example 13 | Ti sintered form | Pink | 0.24 |
| Example 14 | Ti sintered form | Gold | 0.25 |
| Example 15 | Ti sintered form | Silver White | 0.24 |
| Comparative Example 4 | Stainless Casting | No Color | 1.23 |

Colored layers are formed by the anodic oxidation method in Examples 16–18. A bracket is attached to an anode and voltage is impressed within a boric acid electrolytic solution to form an oxidation film on the surface of the sintered body. In Examples 16, yellow is obtained with an impression voltage of 10 volts. In Example 17, light blue is obtained with an impression voltage of 40 volts. In Example 18, light green is obtained with an impression voltage of 65 volts. The results of elution measurements of the brackets of Examples 16–18 are summarized in Table 6. The brackets in these Examples are found to possess sufficient characteristics required for orthodontic materials.

TABLE 6

|  | Surface Color | Elution Amount $mg/cm^2$ |
|---|---|---|
| Example 16 | Yellow | 0.26 |
| Example 17 | Light blue | 0.25 |
| Example 18 | Light green | 0.26 |

Colored layers are formed by a heat treatment method in Examples 19 and 20. Heat treatment is conducted on a bracket under atmospheric pressure. In Example 19, the color of yellow-green is obtained with 10 minutes of heat treatment at 500° C., but the layer is thin with interference color appearing. In Example 20, 10 minutes of heat treatment at 1050° C. results in the formation of $TiO_2$ film on the surface of the titanium sintered material, which has a color of yellow-white or white. In this case, the layer is thick and the color of the $TiO_2$ itself appears. The amounts of elution measured in Examples 19 and 20 are presented in Table 7. The brackets in these embodiments are found to possess sufficient characteristics required for orthodontic materials.

TABLE 7

|  | Temperature of Heat Treatment (°C.) | Surface Color | Elution Amount $mg/cm^2$ |
|---|---|---|---|
| Example 19 | 500 | Yellow green | 0.26 |
| Example 20 | 1050 | White | 0.25 |

Colored layers are formed by a heat spraying method in Examples 21 and 22. The spraying of white $Al_2O_3$ (Example 21) powder or white $TiO_2$ (Example 22) powder results in a white surface on the sintered bodies. The amounts of elution measured in Examples 21 and 22 are presented in Table 8. The brackets in these Examples are found to possess sufficient characteristics required for orthodontic materials.

TABLE 8

|  | Spray Material | Surface Color | Elution Amount $mg/cm^2$ |
|---|---|---|---|
| Example 21 | $Al_2O_3$ | White | 0.24 |
| Example 22 | $TiO_2$ | White | 0.26 |

An evaluation was made concerning characteristics of colored layers including the usability of the color, the multiplicity of colors, the bonding strength of the colored layers, the durability of the colored layers, and production costs. The results are presented in Table 9. In the Table, each evaluation is assigned values of 1 to 5 with 5 indicating the most desirable (for production costs, desirable means low cost).

TABLE 9

| Coloring Method | Color |  | Type Color | Color Layer Bonding Strength | Layer Durability | Cost |
|---|---|---|---|---|---|---|
| Ion Plating | 3 |  | 5 | 5 | 5 | 3 |
| Anodic Oxidation | 5 | Bright Color | 5 | 3 | 3 | 4 |
| Heating | 5 | Color close to human tooth | 5 | 2 | 2 | 5 |
| Spraying | 5 | Color close to human tooth | 5 | 2 | 2 | 5 |

As indicated in the table, although the resulting types of colors formed by the ion plating method are not necessarily the most desirable for dental care materials, the ion plating method produces a layer with a high level of colored layer bonding strength and a high degree of durability, making layers formed by the ion plating method the best overall colored dental care material. The anodic oxidation method produces the most colorful layers with bonding strength and production costs rating fair. Layers formed by the heat treatment method and the spraying method show slightly poorer bonding strength and durability, but they were superior in producing colors closest to the real tooth.

While this invention has been described in conjunction with specific embodiments thereof, it is evident that many alternatives, modifications and variations will be apparent to those skilled in the art. Accordingly, the preferred embodiments of the invention as set forth herein are intended to be illustrative, not limiting. Various changes may be made without departing from the spirit and scope of the invention as defined in the following claims.

What is claimed is:

1. A dental care member comprising a sintered body wherein a mixture of titanium powder and an organic binder is made into a molded body that is sintered after binder removal, wherein said sintered body has a carbon content of greater than 0.1% by weight and is molded as an orthodontic bracket or as a dental implant material.

2. The dental care member according to claim 1, wherein the sintered body is molded as dental implant material.

3. The dental care member according to claim 2, wherein the sintered body has a carbon content of no more than 0.5% by weight.

4. The dental care member according to claim 2, wherein the sintered body has an oxygen content of no more than 0.8% by weight.

5. The dental care member according to claim 2, wherein the sintered body has a combined carbon and oxygen content of no more than 1.0% by weight.

6. The dental care member according to claim 2, wherein the sintered body comprises titanium powder having an average granule size of no more than 40 μm in diameter.

7. The dental care member according to claim 2, further comprising a colored layer formed on a surface of the sintered body.

8. The dental care member according to claim 7, further comprising a gold layer or a gold-palladium alloy layer formed over the colored layer.

9. A dental care member comprising a sintered body wherein a mixture of titanium powder and an organic binder is made into a molded body that is sintered after binder removal, wherein the sintered body has a carbon content of greater than 0.1% by weight and is molded as an orthodontic bracket.

10. The dental care member according to claim 9, wherein the sintered body has a carbon content of no more than 0.5% by weight.

11. The dental care member according to claim 9, wherein the sintered body has an oxygen content of no more than 0.8% by weight.

12. The dental care member according to claim 9, wherein the sintered body has a combined carbon and oxygen content of no more than 1.0% by weight.

13. The dental care member according to claim 9, wherein the sintered body comprises titanium powder having an average granule size of no more than 40 μm in diameter.

14. The dental care member according to claim 9, further comprising a colored layer formed on a surface of the sintered body.

15. The dental care member according to claim 14, further comprising a gold layer or a gold-palladium alloy layer formed over the colored layer.

16. A dental care member comprising a sintered body including titanium powder and an organic binder, said sintered body being molded as an orthodontic bracket or a dental implant material and having a carbon content of from greater than 0.1% to no more than 0.5% by weight and an oxygen content of no more than 0.8% by weight.

17. The dental care member of claim 16, wherein the sintered body has a combined carbon and oxygen content of no more than 1.0% by weight.

18. The dental care member of claim 16, wherein the titanium powder has an average granule size of no more than 40 μm in diameter.

* * * * *